United States Patent [19]

Betush

[11] 4,108,178

[45] Aug. 22, 1978

[54] PINCH VALVE SYRINGE

[75] Inventor: Frank A. Betush, Santa Monica, Calif.

[73] Assignee: Progessive Machine Products, Inc., Los Angeles, Calif.

[21] Appl. No.: 791,735

[22] Filed: Apr. 28, 1977

[51] Int. Cl.² .............................................. A61M 3/00
[52] U.S. Cl. .................. 128/224; 128/173.1; 32/22
[58] Field of Search ...................... 128/224, 229, 173.1; 32/22, 24; 137/605-614

[56] References Cited

U.S. PATENT DOCUMENTS

| 3,121,426 | 2/1964 | Yoshida ................................. 128/224 |
| 3,375,823 | 4/1968 | Pamplin et al. ................... 128/173.1 |
| 3,698,088 | 10/1972 | Austin, Jr. ............................... 32/22 |

FOREIGN PATENT DOCUMENTS 1,586,087  2/1970  France ..................................... 128/2 F Primary Examiner—John D. Yasko
Attorney, Agent, or Firm—Keith D. Beecher

[57] ABSTRACT

A syringe is provided which is particularly useful in dental work for emitting a stream of water and air under high pressure into the patient's mouth. The syringe of the invention is simplified as compared with the prior art syringes in that it uses pinch valves to perform its intended functions.

9 Claims, 2 Drawing Figures

PINCH VALVE SYRINGE

BACKGROUND OF THE INVENTION

The prior art syringes usually include pushbutton valves to control the flow of streams of compressed air and water to a nozzle which is mounted on one end of the instrument, the valves being sealed by O-rings. Apart from being complex and expensive, the prior art syringes have a tendency to stick due to debris and/or droppage. The syringe of the present invention on the other hand, which uses pinch valves, is rugged in its construction, simple in its operation, inexpensive and uncomplicated, and it has no tendency to stick, even when subjected to rough usage. Moreover, the syringe of the present invention is reliable in operation, and its life span can be extended merely by moving the tubing therein slightly to produce new pinch points when the previous pinch points show signs of wear, this being achieved without any need to disassemble the instrument or to provide new parts.

It will be evident as the description proceeds that although the pinch valves used in the instrument to be described are particularly suited to enable the instrument to perform a syringe function, the pinch valves may be used in other applications wherever a particular fluid flow control through one or more flexible tubes is desired.

DETAILED DESCRIPTION OF THE ILLUSTRATED EMBODIMENT

Figure 1:
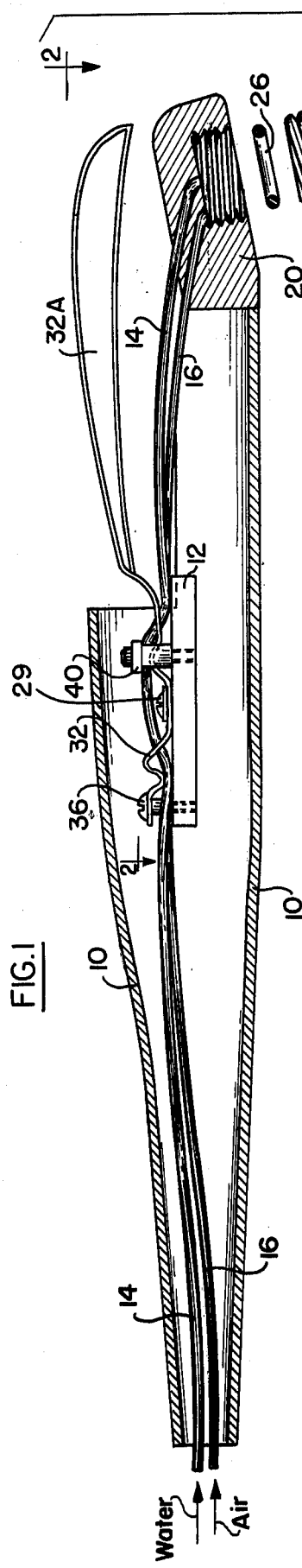
FIG. 1 is a side view, partly in section, of a syringe constructed to incorporate the concepts of the present invention.

As shown in FIG. 1, the syringe includes an elongated hollow tubular body 10 which has a shape to facilitate holding the instrument in the hand of the operator. A base or mounting block 12 is mounted within the tubular body 10 at approximately the midpoint of the instrument, so as to be removable to gain access to its working parts for inspection and adjustments.

A first flexible tube 14 which is intended to carry water, or other fluids, and a second flexible tube 16 which is intended to carry compressed air, or other gases, extend through the tubular body 10 from one end to the other, and through a series of pinch valves. The pinch valves are mounted on block 12, and which will be described subsequently.

The tubes 14 and 16 are coupled to the right-hand end of the instrument to a fitting 20. The fitting 20 receives a nozzle 22, the nozzle being mounted in the fitting by means, for example, of a mounting nut 24; the compressed air received from tube 16 being sealed from the water received from tube 14 by an O-ring 26. The water is carried down a central tube 22A in the nozzle 22, and the air is carried through an annular passage 22B in the nozzle, so that air and water are emitted at high pressure from the end of the nozzle. The nozzle construction is in accordance with usual prior art practice, permitting nozzle 22 to swivel inside nut 24 to conveniently direct the output flow. In embodiments not requiring this swivel, tubes 14 and 16 may run continuously to the tip of the nozzle without the need for O-ring 26.

A pair of elongated resilient strips 30 and 32 are mounted on the mounting block 12 in transversely spaced relationship with respect to one another. A mounting screw 28, and associated eccentric washer, serve to affix an intermediate point of strip 30 to the mounting block, and a mounting screw 29, and associated eccentric washer, serve to affix an intermediate point of strip 32 to the mounting block. Each of the strips has a first bend formed therein adjacent the left end thereof designated X—X in FIG. 2, and which extends toward the mounting block, as best shown in FIG. 1. The left ends of strips 30 and 32 are held down by respective screws 34, 36; and the downward bias of the X bends may be adjusted by adjusting these screws. Also, each strip 30, 32 has a second bend therein extending away from the mounting block as also shown in FIG. 1, the second bends being designated Y in FIG. 2. The upward bias of the Y bends may be adjusted by rotating the eccentric washers associated with screws 28 and 29.

Figure 2:
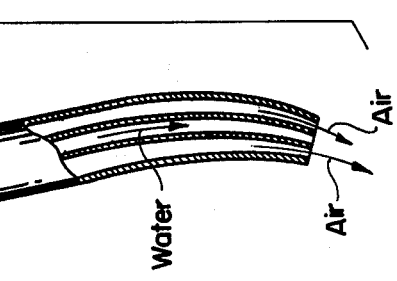
FIG. 2 is a view taken essentially along the line 2—2 of FIG. 1.
Figure 2:
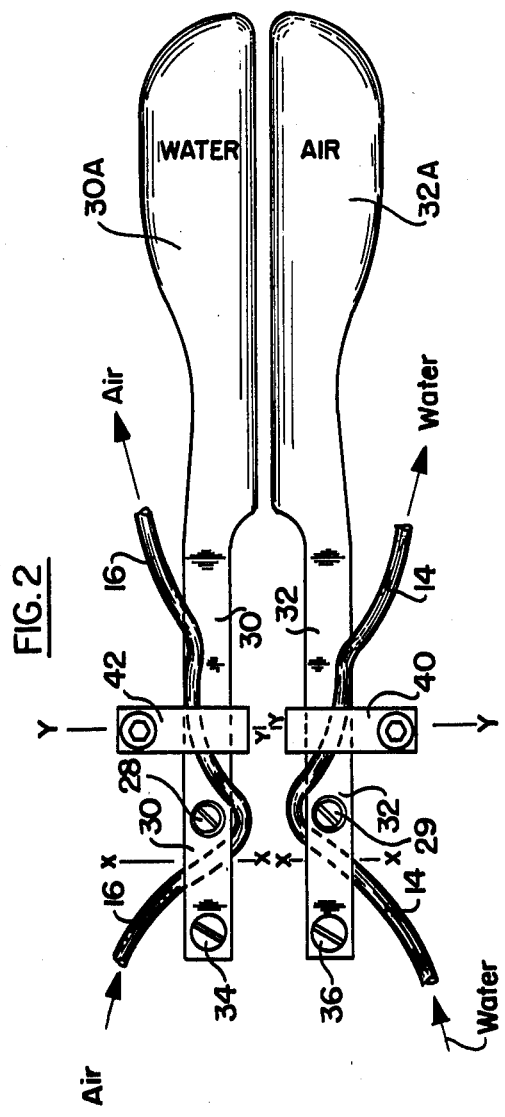

A first rigid arm 40 is mounted on the mounting block 12 in spaced relationship from the block, and extends across the Y bend in strip 30. Likewise, a rigid arm 42 is mounted on the mounting block in spaced relationship from the top surface of the block, and it extends across the Y bend in strip 32. The water tube 14 extends under the strip 30 between the X bend and mounting block 12, and also extends across the strip between the arm 40 and Y bend. Likewise, the air tube 16 extends under the strip 32 between the X bend and mounting block 12, and over strip 32 between the Y bend and arm 42, as best shown in FIG. 2.

The X bends in the strips 30 and 32 pinch the water and air tubes 14 and 16 partially to close the tubes. The amount of pinching effect for each tube is controlled by adjusting the screws 34 and 36, so that the rate of flow of air and water through the respective tubes may be controlled by setting the screws 34 and 36. In the normal position of the strips 30 and 32, the tubes 14 and 16 are pinched closed by the respective arms 40 and 42, so that no air or water flows to the nozzle 22.

The ends of strips 30 and 32 are formed into handles 30A and 32A which form effective pushbutton controls, and which may indicate by appropriate markings what is dispensed for example, air and water. Their form may be suitable for convenient operation from many attitudes.

When either handle 30A or 32A is squeezed against the tubular body 10, the tubes 14 and 16 are released from between the arms 40 and 42 and the Y bends in the resilient strips 30 and 32, so that water and air flow to the nozzle in a variable amount, with maximum flow being established by the settings of screws 34 and 36. Depressing both handles produces an atomized mixed stream which can be proportioned variably, in accordance with the operator's applied pressure on handles 30A and 32A to limits set by screws 34 and 36.

Although the syringe shown in FIGS. 1 and 2 provides pinch valve controls for both the air and water line, a single pinch valve control could be provided for one of the lines only, if so desired, with control for the other line being achieved by any appropriate external valve. Alternately, a multiplicity of pinch valve controlled lines could be provided to proportion the dispensed fluids and/or gases as adjusted with settings of screws 34 and 36 on the illustrated embodiment.

As stated above, although the pinch valves of FIGS. 1 and 2 are shown in conjunction with a particular type of syringe, it will be appreciated that the valves can be used whenever a like control of fluid through a flexible tube, or tubes, is desired.

Therefore, although a particular embodiment of the invention has been shown and described, modifications may be made. It is intended in the claims to cover the modifications that come within the spirit and scope of the invention.

What is claimed is:

1. A unit for controlling the flow of a fluid including: a base; an elongated resilient strip having a first bend therein adjacent a first end thereof and extending toward said base and having a second bend therein extending away from said base; an arm mounted on said base in a position displaced from the base and extending across said second bend in said strip, said second bend being normally biased by said strip towards said arm; a flexible tube extending between the base and the first bend in said strip to be pinched thereby and further extending between the arm and the second bend to be further pinched thereby; means attaching said first end of said strip to said base to establish the amount of pinching of the tube by said first bend so as to establish the rate of flow of fluid through the tube; and means at the other end of said strip to move the strip toward the base and away from the arm so as to release the tube from the pinching effect of said second bend and said arm.

2. The unit defined in claim 1, in which said attaching means is adjustable.

3. The unit defined in claim 1, in which said last-named means comprises a handle formed integral with the other end of the strip.

4. The unit defined in claim 1, in which said attaching means comprises a screw threaded into said base and adjustable to control the amount of pinching of the tube by said first bend thereby to control the rate of flow of fluid through the tube.

5. The unit defined in claim 1, and which includes an elongated tubular body enclosing said base, and a nozzle mounted at one end of said body to receive pressurized fluid from the tube, so that the unit may function as a syringe.

6. The unit defined in claim 2, and which includes means adjustably mounting an intermediate point of said strip to said base to control the upward bias of said second bend of said strip toward said arm.

7. The unit defined in claim 1, and which includes a second elongated resilient strip mounted on said base adjacent to the first-mentioned elongated resilient strip and having a first bend therein adjacent to a first end thereof and extending toward said base and further having a second bend therein extending away from said base; a second arm mounted on said base in a position displaced from the base and extending across the second bend in the second strip, the second bend of the second strip being normally biased by said second strip toward said second arm; a second flexible tube extending between the base and the first bend in said second strip to be pinched thereby, and also extending between the second arm and the second bend in the second strip further to be pinched thereby; means affixing the first end of the second strip to the base to establish the amount of pinching of the second tube by the first bend therein so as to establish the rate of flow of fluid through the second tube; and means at the other end of the second strip to move the second strip toward the base and away from the second arm to release the second tube from the pinching effect of the second bend in the second strip and said second arm.

8. The unit defined in claim 5, and which includes an elongated tubular body enclosing said base, and a nozzle mounted at one end of the body for receiving pressurized fluids from the tubes.

9. The unit defined in claim 6, in which one of the tubes carries compressed air and the other of the tubes carries water to the nozzle so that the unit may function as a syringe.

* * * * *